(12) United States Patent
Maswadeh et al.

(10) Patent No.: US 6,840,456 B1
(45) Date of Patent: Jan. 11, 2005

(54) INJECTION VALVES

(75) Inventors: Waleed M. Maswadeh, Rosedale, MD (US); A. Peter Snyder, Bel Air, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 219 days.

(21) Appl. No.: 10/241,163

(22) Filed: Sep. 11, 2002

(51) Int. Cl.⁷ .............................................. B05B 17/00
(52) U.S. Cl. .................. 239/1; 239/533.1; 239/584; 73/23.41; 95/86
(58) Field of Search ................ 239/1, 533.1, 583–586; 73/23.41, 23.42, 864.85, 864.87; 95/86, 89, 87; 96/105

(56) References Cited

U.S. PATENT DOCUMENTS

| | | | |
|---|---|---|---|
| 4,019,863 A | * | 4/1977 | Jenkins et al. ............... 250/304 |
| 4,461,183 A | * | 7/1984 | Wedding ................. 73/863.21 |
| 4,970,905 A | | 11/1990 | McClennen et al. |
| 4,977,785 A | * | 12/1990 | Willoughby et al. ...... 73/863.12 |

* cited by examiner

Primary Examiner—Dinh Q. Nguyen
(74) Attorney, Agent, or Firm—Ulysess John Biffoni

(57) ABSTRACT

An injection valve is provided. A first conduit is disposed between first and second chambers of the valve. An entrance to the first conduit is located within the first chamber. A second conduit is concentrically disposed within the first conduit so that there is a first flow passage between the first and second conduits connecting the first and second chambers. The second conduit has an entrance communicating with the first chamber via the entrance of the first conduit and an exit defining a first outlet port of the valve. A cover opens and closes a first inlet port of the first chamber, and a biasing device biases the cover closed. An actuator moves the cover from the closed position to open the first inlet port.

25 Claims, 8 Drawing Sheets

INJECTION VALVES

TECHNICAL FIELD

The present invention relates generally to the field of valves and, in particular, to injection valves.

BACKGROUND

In many gas chromatography methods a sample fluid, such as a gas or liquid, is injected into an entrance of a chromatography column using a syringe. Typically the syringe is inserted through a septum that is separated from the column entrance by a ballast region, for example. However, the distance between the septum and the column entrance is too large in that the sample has an opportunity to stick to surfaces of the ballast region, causing sample degradation. Moreover, as the sample is injected from the syringe into the ballast region, the sample usually expands, causing dilution of the sample.

For the reasons stated above, and for other reasons stated below that will become apparent to those skilled in the art upon reading and understanding the present specification, there is a need in the art for alternatives for injecting sample fluids into chromatography columns.

SUMMARY

The above-mentioned problems with injecting sample fluids into chromatography columns and other problems are addressed by embodiments of the present invention and will be understood by reading and studying the following specification.

In one embodiment, an injection valve having first and second chambers is provided. A first conduit is disposed between the first and second chambers. An entrance to the first conduit is located within the first chamber. A second conduit is concentrically disposed within the first conduit so that there is a first flow passage between the first and second conduits connecting the first and second chambers. The second conduit has an entrance communicating with the first chamber via the entrance of the first conduit and an exit defining a first outlet port of the valve. The injection valve includes a cover for opening and closing a first inlet port of the first chamber. A biasing device for biasing the cover in a first position, where the cover closes the first inlet port of the first chamber, is also included. The injection valve includes an actuator for selectively moving the cover from the first position to selectively open the first inlet port of the first chamber.

Other embodiments are described and claimed.

DETAILED DESCRIPTION

In the following detailed description, reference is made to the accompanying drawings that form a part hereof, and in which is shown by way of illustration specific illustrative embodiments in which the invention may be practiced. These embodiments are described in sufficient detail to enable those skilled in the art to practice the invention, and it is to be understood that other embodiments maybe utilized and that logical, mechanical and electrical changes may be made without departing from the spirit and scope of the present invention. The following detailed description is, therefore, not to be taken in a limiting sense.

Figure 1:
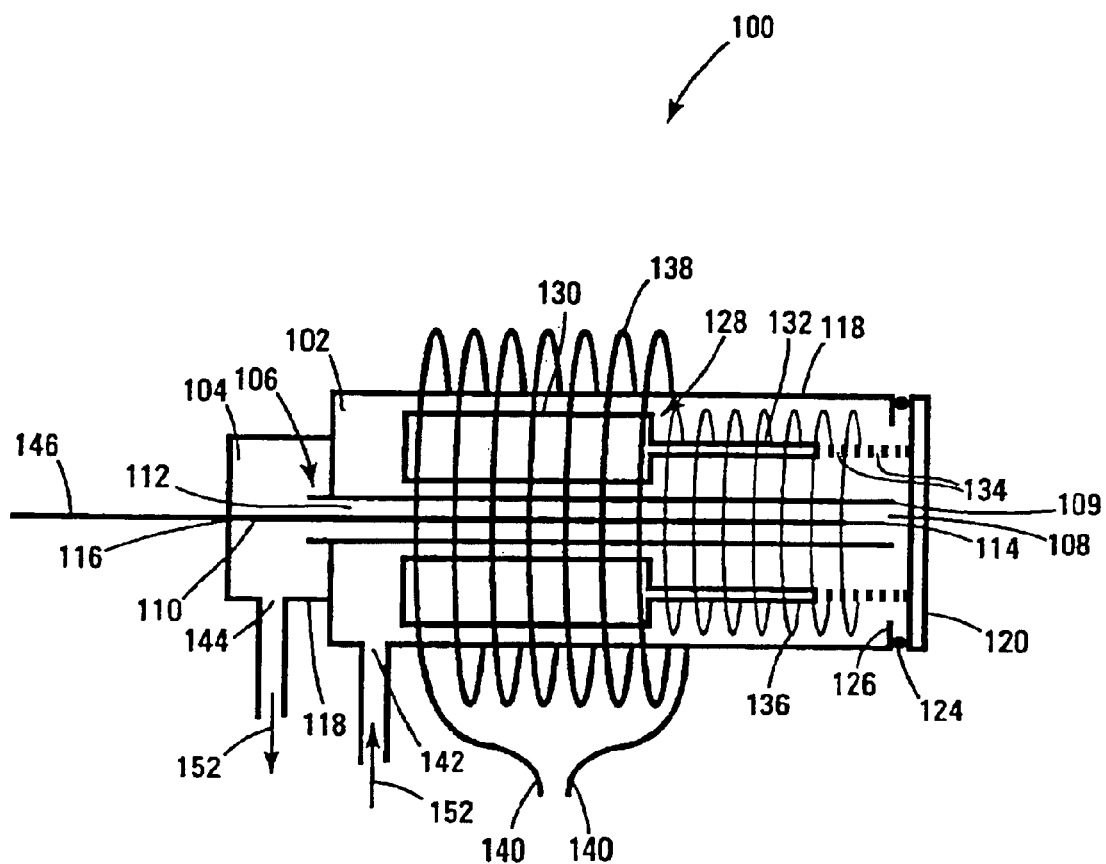
FIGS. 1 and 2 respectively illustrate an injection valve in closed and open states according to an embodiment of the present invention.
Figure 2:
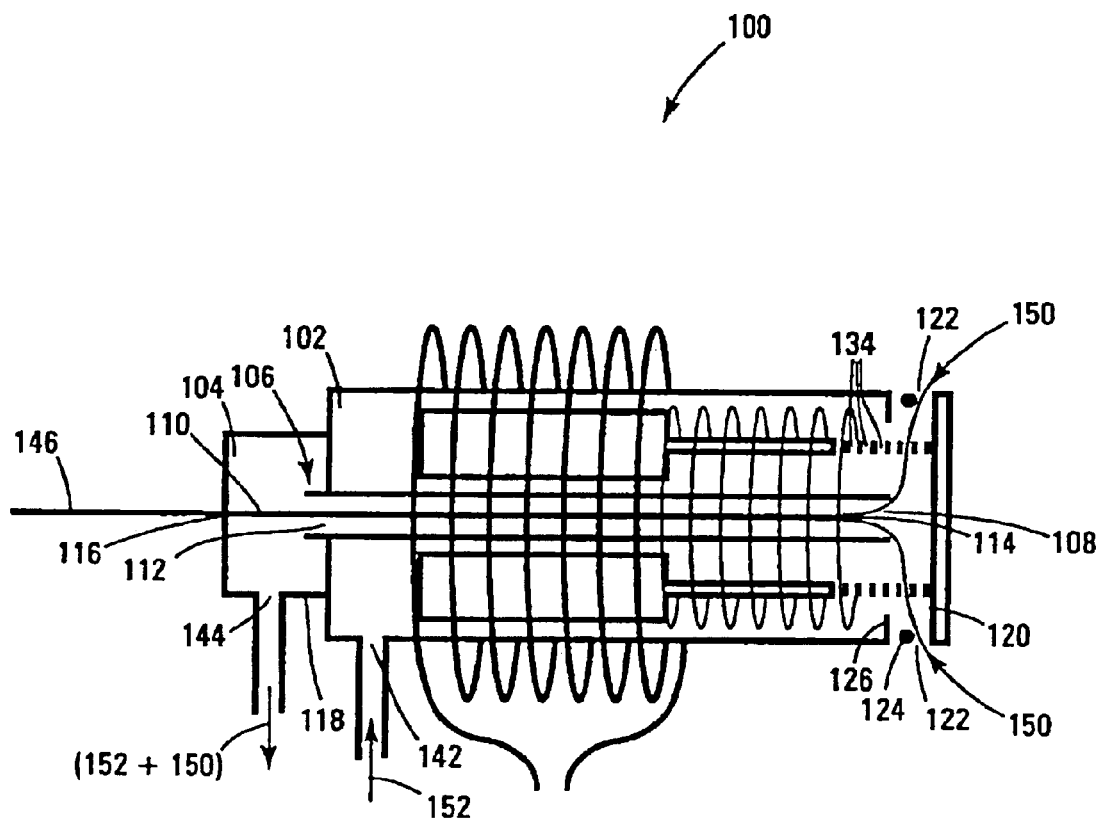

FIGS. 1 and 2 respectively illustrate an injection valve 100 in closed and open states according to an embodiment of the present invention. Injection valve 100 includes chambers 102 and 104. A conduit 106 is disposed between chambers 102 and 104 so that an entrance 108 of conduit 106 is located within chamber 102. In one embodiment, entrance 108 is an opening in an end 109 of conduit 106. A conduit 110 is concentrically disposed within conduit 106 so that there is a flow passage 112 between conduits 106 and 110 connecting chambers 102 and 104. Conduit 110 has an entrance 114 communicating with chamber 102 via entrance 108 of conduit 106 and an exit 116 defining a first outlet port of valve 100. In one embodiment, conduits 106 and 110 have circular, square, rectangular cross-sections, or the like and are of plastic, e.g., TEFLON, metal, e.g., steel, aluminum, or the like. In another embodiment, conduit 110 is a capillary tube, such as used for gas or liquid chromatography.

In one embodiment, chambers 102 and 104 are contained within a housing 118 of valve 100 having a circular, square, rectangular cross-section or the like. In various embodiments, housing 118 is of plastic, e.g., TEFLON, metal, e.g., steel, aluminum, or the like.

Injection valve 100 includes a cover 120 for opening and closing an inlet port 122 of chamber 102 located between a lip 126 of housing 118 and cover 120, as shown in FIG. 2. In one embodiment, cover 120 is located externally to chamber 102 and moves externally to chamber 102 when moving between the closed and open positions respectively shown in FIGS. 1 and 2. In another embodiment, cover 120 abuts a seal 124, such as an O-ring or the like, disposed on lip 126 to seal inlet port 122.

In another embodiment, a piston 128 is positioned concentrically about conduit 106 and is connected to cover 120. In other embodiments, piston 128 includes a base 130 and a connector 132 that connects to cover 120 to base 130, as shown in FIG. 1. In some embodiments, base 130, connector 132, and cover 120 are integral. In one embodiment, connector 132 and cover 120 are attached together by bolting, screwing, welding, or the like. In yet another embodiment, one or more apertures 134 pass through connector 132, as shown in FIGS. 1 and 2.

In some embodiments, a biasing device 136 is disposed concentrically about connector 132 and is located between base 130 and lip 126 for biasing piston 128 in a first position, shown in FIG. 1, so that cover 120 closes inlet port 122 of chamber 102. In one embodiment, biasing device 136 is a spring, a hollow elastomeric cylinder, or the like.

In one embodiment, a wire coil 138, such as a solenoid coil is concentrically disposed around piston 128. When electrical current is selectively supplied to wire coil 138 via lead wires 140, wire coil 138 exerts an electromagnetic force on piston 128. This force moves piston 128 from the first position shown in FIG. 1 to a second position shown in FIG. 2 so that cover 120 selectively opens inlet port 122. Selectively removing the electrical current from lead wires 140 removes the electromagnetic force exerted on piston 128 by wire coil 138 from piston 128, and biasing device 136 moves piston 128 to the first position so that cover 120 closes inlet port 122. In this embodiment, piston 128 is a magnetic conductor, such as steel, or the like.

Chamber 102 has an inlet port 142. Chamber 104 has a port 144 defining an outlet port of valve 100. In one embodiment, exit 116 of conduit 110 is connected to a chromatography column 146, e.g., for gas or liquid chromatography, by a quick connect ferrule, or the like. In another embodiment, conduit 110 is an extension of chromatography column 146.

When injection valve 100 is in the open state shown in FIG. 2, e.g., cover 120 opens port 122, a fluid 150, e.g., gas or liquid, flows through port 122 and into chamber 102. In one embodiment, a fluid 152, e.g., gas or liquid, flows into chamber 102 through inlet port 142 while valve 100 is in the open state. In some embodiments, fluid 150 is a sample fluid, and fluid 152 is a chromatography carrier fluid that is used to elute the sample fluid through chromatography column 146. Fluid 150 flows through apertures 134 of piston 128 and into conduit 106 via entrance 108, as shown in FIG. 2. Fluid 152 also flows into conduit 106 via entrance 108. A portion of fluids 150 and 152 flows through conduit 106 and into conduit 110 via entrance 114 and subsequently flows through conduit 110. Fluids 150 and 152 exit conduit 110 at exit 116 and flow into chromatography column 146. In one embodiment, this injects fluid 150 into chromatography column 146. Another portion of fluids 150 and 152 flows through flow passage 112 into chamber 104 and subsequently exits chamber 104 through port 144. In one embodiment, the flow of fluid 152 is stopped when injection valve 100 is opened, and fluid 152 does not flow as described above while valve 100 is open.

When injection valve 100 is in the closed state, as shown in FIG. 1, cover 120 prevents fluid 150 from flowing into chamber 102 through inlet port 122, and fluid 152 flows into conduit 106. In one embodiment, fluid 152 flows a higher rate when injection valve 100 is closed than when injection valve 100 is open. Fluid 152 flows through conduit 110 and into chromatography column 146. Fluid 152 also flows through flow passage 112 into chamber 104 and exits chamber 104 through port 144.

Figure 3:
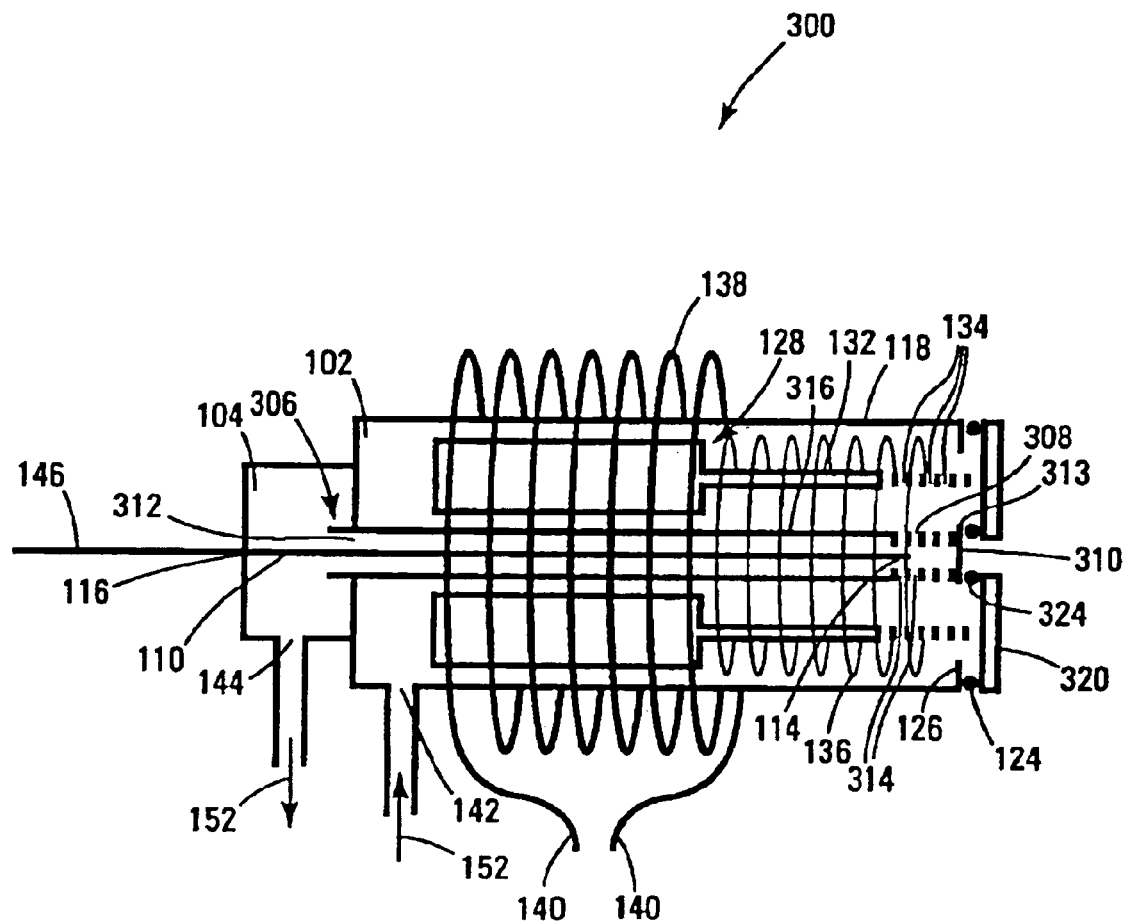
FIGS. 3 and 4 respectively illustrate an injection valve in closed and open states according to another embodiment of the present invention.
Figure 4:
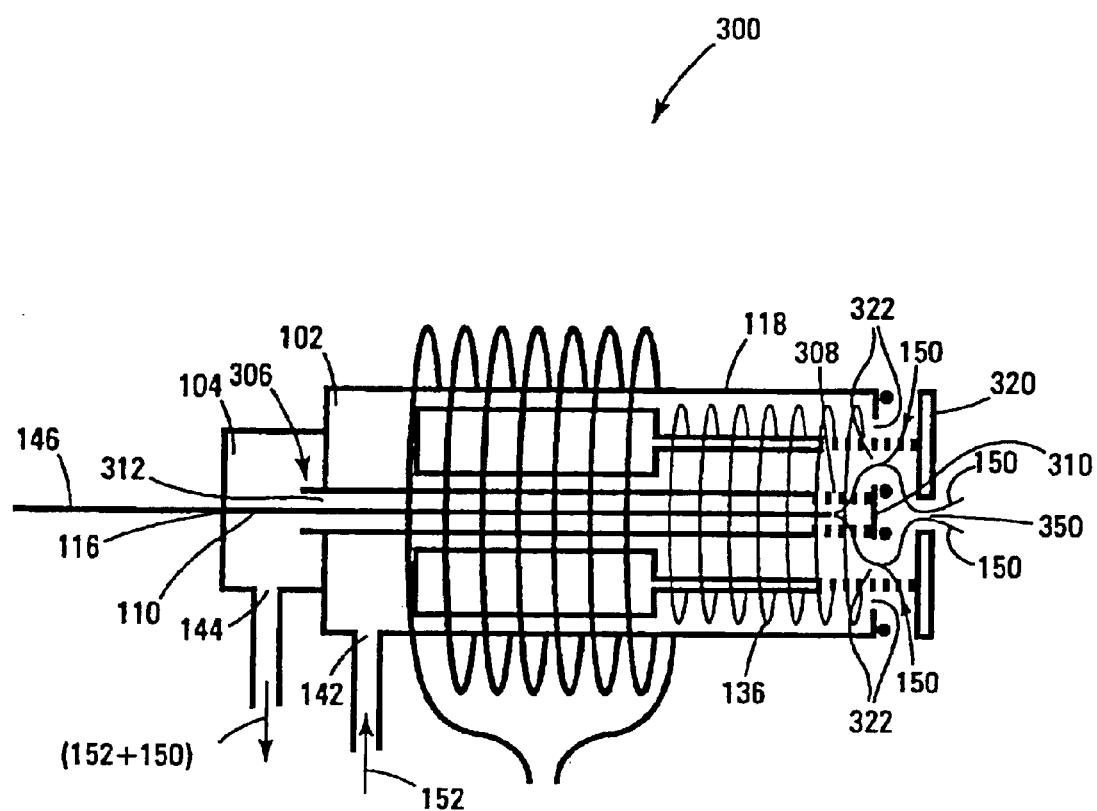

FIGS. 3 and 4 respectively illustrate an injection valve 300 in closed and open states according to another embodiment of the present invention. Elements of FIGS. 3 and 4 that are common with FIGS. 1 and 2 are numbered as in FIGS. 1 and 2 and are as described above. A conduit 306 is disposed between chambers 102 and 104 of injection valve 300 so that an entrance 308 of conduit 306 is located within chamber 102. In one embodiment, conduit 306 includes a cap 310 that closes an end 313 of conduit 106. In this embodiment, entrance 308 comprises a number of holes 314 passing through a wall 316 of conduit 306 adjacent end 313. Conduit 110 is concentrically disposed within conduit 306 so that there is a flow passage 312 between conduits 306 and 110 connecting chambers 102 and 104. Entrance 114 of conduit 110 communicates with chamber 102 via entrance 308 of conduit 306, and exit 116 of conduit 110 defines a first outlet port of valve 300. In one embodiment, conduit 306 has a circular, square, rectangular cross-section, or the like and is of plastic, e.g., TEFLON, metal, e.g., steel aluminum, or the like.

Injection valve 300 includes a cover 320 for opening and closing an inlet port 322, as shown in FIG. 4, of chamber 102. In one embodiment, inlet port 322 is a gap between housing 118 and cap 310 having an annular shape, for example. In another embodiment, cover 320 is located externally to chamber 102 and moves externally to chamber 102 when moving between the closed and open positions respectively shown in FIGS. 3 and 4. In another embodiment, cover 320 abuts seal 124 and a seal 324, such as an O-ring or the like, disposed on cap 310, as shown in FIG. 3, to seal inlet port 322. In one embodiment, piston 128 is positioned concentrically about conduit 306 and is connected to cover 320, as described above for cover 120. Biasing device 136 biases piston 128 in a first position, shown in FIG. 3, so that cover 320 closes inlet port 322 of chamber 102.

When electrical current is selectively supplied to wire coil 138 via lead wires 140, wire coil 138 exerts an electromagnetic force on piston 128. This force moves piston 128 from the first position shown in FIG. 3 to a second position shown in FIG. 4 so that cover 320 selectively opens inlet port 322. Selectively removing the electrical current from lead wires 140 removes the electromagnetic force exerted on piston 128 by wire coil 138 from piston 128, and biasing device 136 moves piston 128 to the first position so that cover 320 closes inlet port 322.

When injection valve 300 is in the open state shown in FIG. 4, fluid 150 flows through inlet port 322, through apertures 134 of piston 128, and into conduit 306 via holes 314 of entrance 308. In one embodiment, fluid 150 also flows through a hole 350 in cover 320 and into conduit 306 via entrance 308, as shown in FIG. 4. Fluid 152 also flows into conduit 306 through holes 314, in another embodiment. A portion of fluids 150 and 152 flows through conduit 110 and into chromatography column 146, while another portion flows through flow passage 312 and is exhausted through port 144. When valve 300 is in the closed position shown in FIG. 3, cover 320 prevents fluid 150 from flowing into chamber 102, and fluid 152 flows into conduit 306 through holes 314. Fluid 152 flows through conduit 110 and into chromatography column 146. Fluid 152 also flows through flow passage 312 into chamber 104 and exits chamber 104 through port 144. In one embodiment, the flow of fluid 152 is stopped when injection valve 300 is opened, and fluid 152 does not flow as described above while valve 300 is open.

Figure 5:
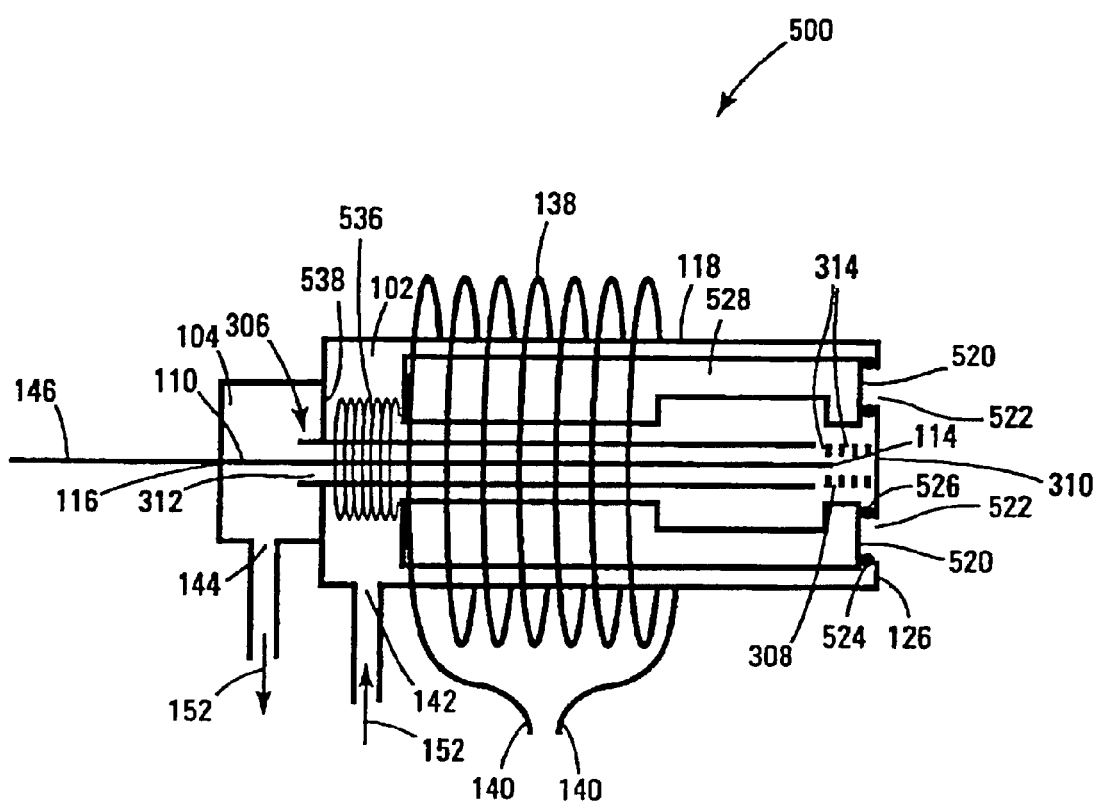
FIGS. 5 and 6 respectively illustrate an injection valve in closed and open states according to yet another embodiment of the present invention.
Figure 6:
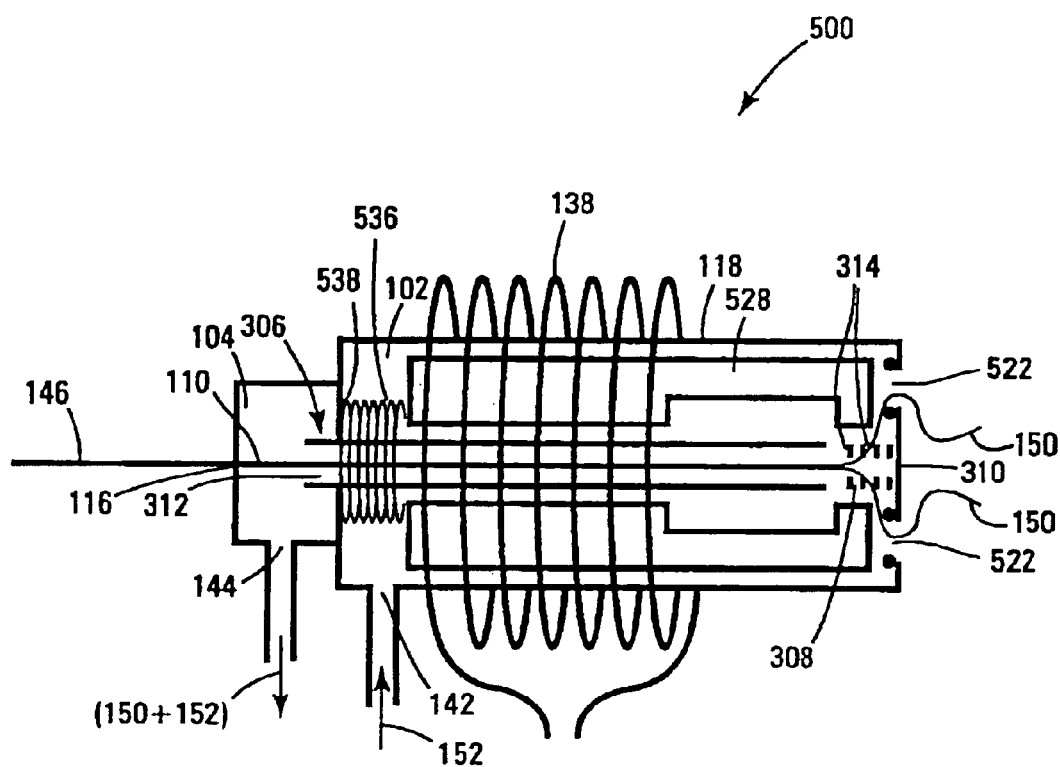

FIGS. 5 and 6 respectively illustrate an injection valve 500 in closed and open states according to another embodiment of the present invention. Elements of FIGS. 5 and 6 that are common with FIGS. 3 and 4 are numbered as in FIGS. 3 and 4 and are as described above. Conduit 306 is disposed between chambers 102 and 104 so that entrance 308 of conduit 306 is located within chamber 102. Conduit 110 is concentrically disposed within conduit 306 so that there is a flow passage 312 between conduits 306 and 110 connecting chambers 102 and 104. Entrance 114 of conduit 110 communicates with chamber 102 via entrance 308 of conduit 306, and exit 116 of conduit 110 defines a first outlet port of valve 500.

Injection valve 500 includes a cover 520 for opening and closing an inlet port 522, as shown in FIGS. 5 and 6, of chamber 102. In one embodiment, inlet port 522 is a gap between housing 118 and conduit 306 having an annular shape, for example. In another embodiment, cover 520 is located within chamber 102 and moves within chamber 102 when moving between the closed and open positions respectively shown in FIGS. 5 and 6. In another embodiment, cover 520 abuts seals 524 and 526, such as O-rings or the like, respectively disposed on lip 126 and cap 310, as shown in FIG. 5, to seal inlet port 522.

In some embodiments, a piston 528 is positioned concentrically about conduit 306 and is connected to cover 520. In one embodiment, cover 520 is integral with piston 528. A biasing device 536 is disposed within chamber 102 between piston 528 and a wall 538 that forms a boundary between chambers 102 and 104, as shown in FIG. 5. Biasing device 538 biases piston 528 in a first position, shown in FIG. 5, so that cover 520 closes inlet port 522 of chamber 102. In one embodiment, biasing device 536 is a spring, a hollow elastomeric cylinder, or the like. In another embodiment, biasing device 536 is concentrically disposed about conduit 306, as shown in FIG. 5.

In one embodiment, wire coil 138 is concentrically disposed around piston 528. When electrical current is selectively supplied to wire coil 138 via lead wires 140, wire coil 138 exerts an electromagnetic force on piston 528. This force moves piston 528 from the first position shown in FIG. 5 to a second position shown in FIG. 6 so that cover 520 selectively opens inlet port 522. Selectively removing the electrical current from lead wires 140 removes the electromagnetic force exerted on piston 528 by wire coil 138 from piston 528, and biasing device 536 moves piston 528 to the first position so that cover 520 closes inlet port 522. In this embodiment, piston 528 is a magnetic conductor, such as steel or the like.

When valve 500 is in the open state shown in FIG. 6, fluid 150 flows through inlet port 522 and into conduit 306 via entrance 308. Fluid 152 also flows into conduit 306 through entrance 308. A portion of fluids 150 and 152 flows through conduit 110 and into chromatography column 146, while another portion flows through flow passage 312 and is exhausted through port 144. When valve 500 is in the closed position shown in FIG. 5, cover 520 prevents fluid 150 from flowing into chamber 102, and fluid 152 flows into conduit 306 through holes 314. Fluid 152 flows through conduit 110 and into chromatography column 146. Fluid 152 also flows through flow passage 312 into chamber 104 and exits chamber 104 through port 144. In one embodiment, the flow of fluid 152 is stopped when injection valve 500 is opened, and fluid 152 does not flow as described above while valve 500 is open.

Figure 7:
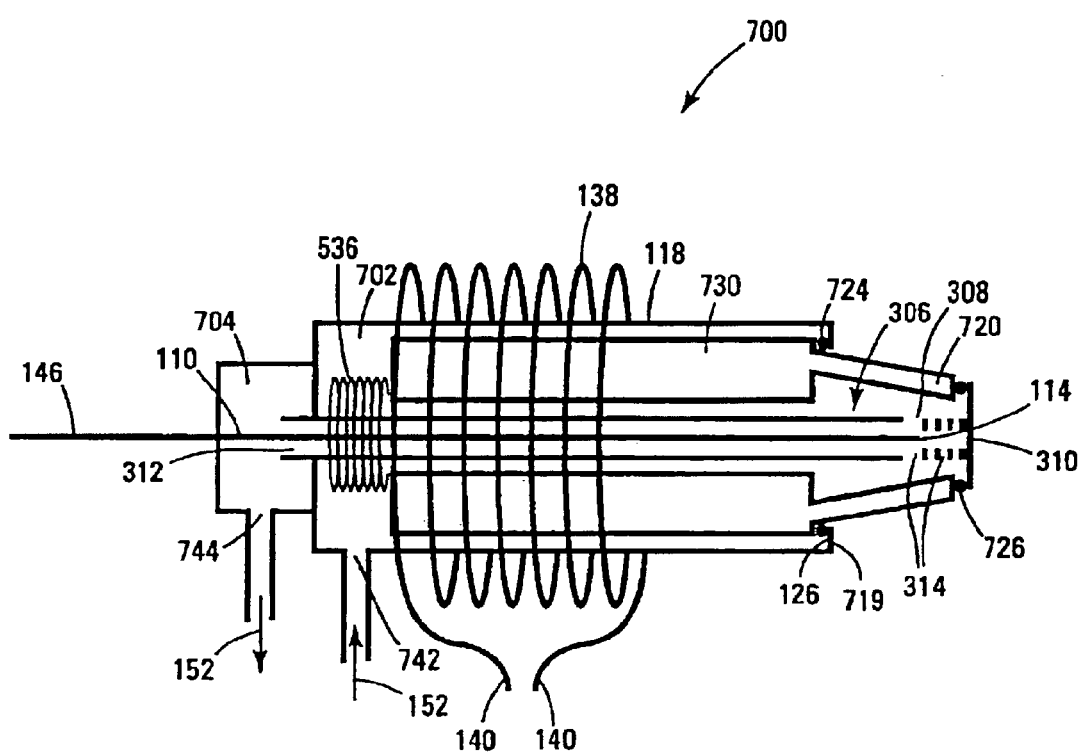
FIGS. 7 and 8 respectively illustrate an injection valve in closed and open states according to still another embodiment of the present invention.
Figure 8:
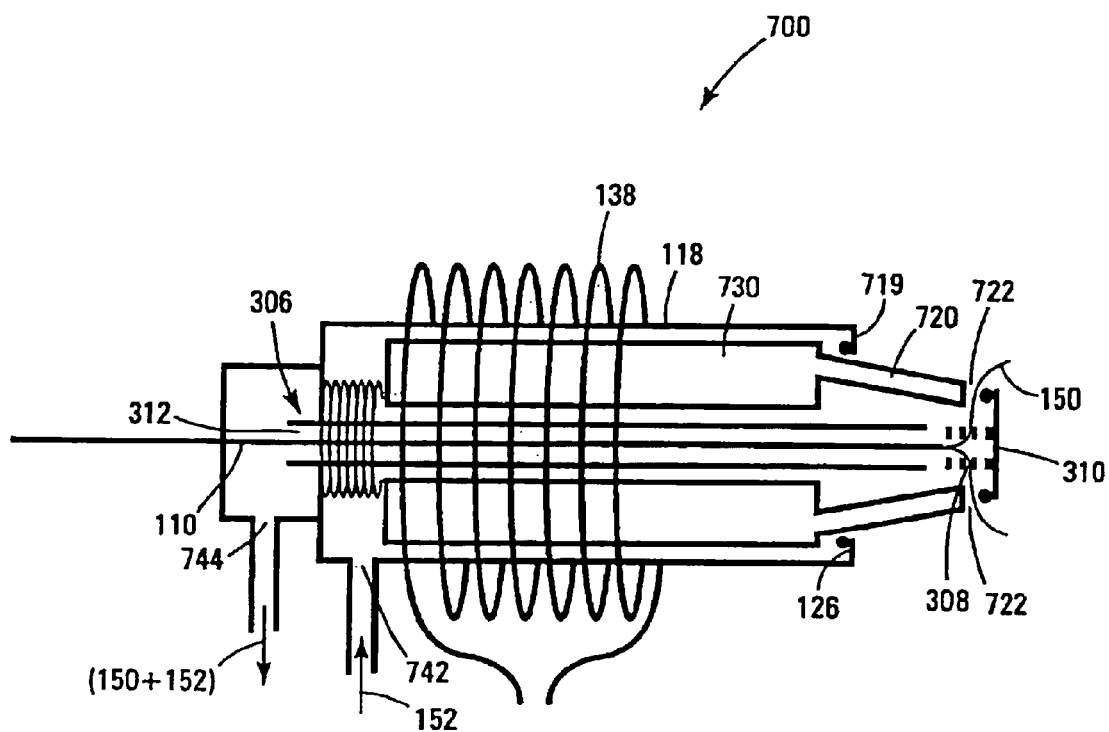

FIGS. 7 and 8 respectively illustrate an injection valve 700 in closed and open states according to another embodiment of the present invention. Elements of FIGS. 7 and 8 that are common with FIGS. 5 and 6 are numbered as in FIGS. 5 and 6 and are as described above. Injection valve 700 includes chambers 702 and 704. Conduit 306 is disposed between chambers 702 and 704 so that entrance 308 of conduit 306 is located within chamber 702. Cap 310 of conduit 306 is offset from housing 118 so that chamber 702 extends beyond an end 719 of housing 118, as shown in FIGS. 7 and 8. Conduit 10 is concentrically disposed within conduit 306 so that there is a flow passage 312 between conduits 306 and 110 connecting chambers 702 and 704. Entrance 114 of conduit 10 communicates with chamber 702 via entrance 308 of conduit 306, and exit 116 of conduit 110 defines a first outlet port of valve 700.

Injection valve 700 includes a cover 720 for opening and closing an inlet port 722, as shown in FIG. 8, of chamber 702. In one embodiment, inlet port 722 is a gap between end 719 of housing 118 and cap 310. In another embodiment, cover 720 abuts seals 724 and 726, such as O-rings or the like, respectively disposed on a lip 126 and cap 310, as shown in FIG. 7, to seal inlet port 722.

In some embodiments, a piston 730 is positioned concentrically about conduit 306 and is connected to cover 720. In one embodiment, cover 720 is integral with piston 730. Biasing device 536 biases piston 730 in a first position, shown in FIG. 7, so that cover 720 closes inlet port 722 of chamber 702. In one embodiment, wire coil 138 is concentrically disposed around piston 730. When electrical current is selectively supplied to wire coil 138 via lead wires 140, wire coil 138 exerts an electromagnetic force on piston 730. This force moves piston 730 from the first position shown in FIG. 7 to a second position shown in FIG. 8. This moves cover 720 into housing 118, causing cover 720 to selectively open inlet port 722. Selectively removing the electrical current from lead wires 140 removes the electromagnetic force exerted on piston 730 by wire coil 138 from piston 730, and biasing device 536 moves piston 730 to the first position so that cover 720 closes inlet port 722. In this embodiment, piston 730 is a magnetic conductor, such as steel, or the like.

When valve 700 is in the open state shown in FIG. 8, fluid 150 flows through inlet port 722 and into conduit 306 via entrance 308. Fluid 152 also flows into conduit 306 through an inlet port 142 of chamber 702. A portion of fluids 150 and 152 flows through conduit 110 and into chromatography column 146, while another portion flows through flow passage 312 and is exhausted through a port 744 of chamber 704, defining an outlet port of valve 700. When valve 700 is in the closed position shown in FIG. 7, cover 720 prevents fluid 150 from flowing into chamber 702, and fluid 152 flows into conduit 306 through holes 314. Fluid 152 flows through conduit 110 and into chromatography column 146. Fluid 152 also flows through flow passage 312 into chamber 104 and exits chamber 104 through port 744. In one embodiment, the flow of fluid 152 is stopped when injection valve 700 is opened, and fluid 152 does not flow as described above while valve 700 is open.

CONCLUSION

Embodiments of the present invention have been described. The embodiments provide injection valves. In one embodiment, the injection valves are connectable to a chromatography column for injecting a sample fluid into the chromatography column.

Although specific embodiments have been illustrated and described in this specification, it will be appreciated by those of ordinary skill in the art that any arrangement that is calculated to achieve the same purpose may be substituted for the specific embodiment shown. This application is intended to cover any adaptations or variations of the present invention. For example, fluid power can be used to move piston 128, piston 528, or 728 instead of electrical power via wire coil 138. It is manifestly intended that this invention be limited only by the following claims and equivalents thereof.

What is claimed is:

1. An injection valve comprising:

first and second chambers;

a first conduit disposed between the first and second chambers, an entrance to the first conduit located within the first chamber, a second conduit concentrically disposed within the first conduit so that there is a first flow passage between the first and second conduits connecting the first and second chambers, the second conduit having an entrance communicating with the first chamber via the entrance of the first conduit and an exit defining a first outlet port of the valve;

a cover for opening and closing a first inlet port of the first chamber, a biasing device for biasing the cover in a first position where the cover closes the first inlet port of the first chamber; and an actuator for selectively moving the cover from the first position to selectively open the first inlet port of the first chamber.

2. The injection valve of claim 1, wherein the first outlet port of the valve is connectable to a gas chromatography column.

3. The injection valve of claim 1, wherein the actuator comprises a solenoid.

4. The injection valve of claim 1, wherein the cover is connected to a piston.

5. The injection valve of claim 4, wherein the piston is disposed concentrically about the first conduit.

6. The injection valve of claim 1, wherein the first chamber has a second inlet port and the second chamber has a port defining a second outlet port of the valve.

7. The injection valve of claim 1, wherein the biasing device is a spring.

8. The injection valve of claim 1, wherein the entrance to the first conduit comprises a plurality of holes passing through a wall of the conduit.

9. The injection valve of claim 1, wherein the entrance to the first conduit is an opening in an end of the first conduit.

10. The injection valve of claim 1, wherein the second conduit is a capillary tube.

11. The injection valve of claim 1, wherein the second conduit is an extension of a gas chromatography column.

12. An injection valve comprising:
   first and second chambers, the first chamber having first and second inlet ports, the second chamber having a port defining a first outlet port of the valve;
   a first conduit disposed between the first and second chambers, an entrance to the first conduit located within the first chamber;
   a second conduit concentrically disposed within the first conduit so that there is a first flow passage between the first and second conduits connecting the first and second chambers, the second conduit having an entrance communicating with the first chamber via the entrance of the first conduit and an exit defining a second outlet port of the valve;
   a piston positioned concentrically about the first conduit;
   a cover connected to the piston;
   a biasing device for biasing the piston in a first position so that the cover closes the first inlet port of the first chamber; and
   an actuator for selectively moving the piston from the first position to a second position so that the cover selectively opens the first inlet port of the first chamber.

13. The injection valve of claim 12, wherein the actuator comprises a wire coil concentrically disposed around the piston for exerting an electromagnetic force on the piston to move the piston when electrical current is selectively supplied to the wire coil.

14. The injection valve of claim 12, wherein the second outlet port of the valve is connectable to a gas chromatography column.

15. The injection valve of claim 12, wherein the biasing device is a spring.

16. The injection valve of claim 12, wherein the biasing device is concentrically disposed about the first conduit.

17. The injection valve of claim 12, wherein the entrance to the first conduit comprises a plurality of holes passing through a wall of the conduit.

18. The injection valve of claim 12, wherein the entrance to the first conduit is an opening in an end of the first conduit.

19. The injection valve of claim 12, wherein the piston comprises one or more apertures for providing a fluid flow path between the first inlet port of the first chamber and the entrance to first conduit.

20. The injection valve of claim 12, wherein the second conduit is an extension of a gas chromatography column.

21. A method for injecting a sample fluid into a column, comprising:
   selectively moving a cover of an injection valve from a closed position to an open position to selectively open an inlet port of the injection valve using a piston of the injection valve;
   receiving the sample fluid at the inlet port;
   directing the sample fluid from the inlet port to an entrance of a first conduit disposed within the injection valve;
   directing the sample fluid from the entrance of the first conduit through the first conduit to an entrance of a second conduit concentrically disposed within the first conduit; and
   directing the sample fluid through the second conduit into the column.

22. The method of claim 21, wherein directing the sample fluid from the inlet port to the entrance of the first conduit comprises the sample fluid flowing through one or more apertures in the piston.

23. The method of claim 21, wherein directing the sample fluid from the inlet port to the entrance of the first conduit comprises the sample fluid flowing through a plurality holes in a wall of the first conduit.

24. The method of claim 21, wherein selectively moving the cover of the injection valve from the closed position to the open position comprises using an electromagnetic force to move the piston.

25. The method of claim 24, wherein using an electromagnetic force to move the piston comprises using a solenoid.

* * * * *